United States Patent [19]

Morse et al.

[11] Patent Number: 5,478,724
[45] Date of Patent: Dec. 26, 1995

[54] LENTIVIRUS-SPECIFIC NUCLEOTIDE PROBES AND METHODS OF USE

[75] Inventors: Stephen S. Morse; Irwin H. Gelman; Hidesaburo Hanafusa, all of New York, N.Y.

[73] Assignee: The Rockefeller University, New York, N.Y.

[21] Appl. No.: 147,011

[22] Filed: Oct. 29, 1993

Related U.S. Application Data

[63] Continuation of Ser. No. 746,706, Aug. 16, 1991, abandoned.

[51] Int. Cl.$^6$ .............................. C12Q 1/70; C12Q 1/68; C07H 21/00; C07H 21/04
[52] U.S. Cl. .................. 435/5; 435/6; 435/91.2; 435/810; 435/501; 536/23.1; 536/24.1; 536/24.3; 536/24.31; 536/24.32; 536/24.33; 935/77; 935/78
[58] Field of Search ................... 435/5, 6, 91.2, 435/810; 436/501; 536/22.1, 23.1, 24.1, 24.31–24.33; 935/77.78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,822,731 | 4/1989 | Watson et al. | 435/6 |

FOREIGN PATENT DOCUMENTS

0269445A2  1/1988  European Pat. Off. .

OTHER PUBLICATIONS

M. Saltarelli et al. Virology 179, 347–364 (1990).
A. Haase et al. Proc. Natl. Acad. Sci. USA 87, 4971–4975 (1990).
F. R. Kramer and P. M. Lizardi Nature 339, 401–402 (1989).
K. J. Garvey et al. Virology 175, 391–409 (1990).
M. O. Dayhoff in "Atlas of Protein Sequence and Structure", (ed. M. D. Jayhoff) Natl. Biomed. Res. Foundation 5 (Suppl. 3), 1–8 (1979).
L. Chakrabarti et al. Nature 328, 543–547 (1987).
R. L. Talbott et al. Proc. Natl. Acad. Sci. USA 86, 5743–5747 (1989).
Gonda, et al. Nature 330:388–391 (1987).
Mack and Sninsky Proc. Natl. Acad. Sci. 85;6977–6981 (1988).
Shih et al. J. Virology 63:64–75 (1989).
Doolittle et al. Quart. Rev. Biol. 64:1–30 (1989).
PCR Protocols, A Guide to Methods and Applications, Chapters 5, 40 and 45, Innis, Gelfand, Sninsky, eds., Academic Press, Inc. (1990).
Barber et al. Aids Res. Human Retroviruses 6:1061–1072 (1990).
Davies et al. Science 252:88–95 (1991).
Ou et al. Science 239:295–297 (1988).
De and Srinivasan Oncogene 4:1533–1535 (1989).
Donehower et al. J. Virol. Methods 28:33–46 (1990).

(List continued on next page.)

Primary Examiner—W. Gary Jones
Assistant Examiner—Ardin H. Marschel
Attorney, Agent, or Firm—Arnall Golden & Gregory

[57] ABSTRACT

Nucleic acid oligonucleotide probes or primers that hybridize specifically and exclusively to two regions of the pol gene, identified as LV I and LV II, conserved among a wide range of lentiviruses, wherein the preferred amino acid sequences of the conserved regions are:

$$PHPX_1GLX_2KX_3X_3X_4X_5T$$

wherein $X_1$=A, P or G, $X_2$=K or A, $X_3$=K or R, $X_4$=S or R, and $X_5$=V or I; and $$WX_1GX_2X_3LX_4PX_5KWX_6$$

wherein $X_1$=M, L or I; $X_2$=Y, F or T; $X_3$=E or Q; $X_4$=H or W; $X_5$=D or T; and $X_6$=T or K. Methods of use of the probes and primers in the detection of lentiviral genomic sequences in biological samples and the termination of replication of lentiviruses are also included.

37 Claims, 5 Drawing Sheets

OTHER PUBLICATIONS

Landegren et al. *Science* 242:229–237 (1988).
Landegren et al. *Science* 241:1077–1080 (1988).
Compton *Nature* 350:91–92 (1991).
Kwoh et al. *Proc. Natl. Acad. Sci.* 1173–1177 (1989).
Wu and Wallace *Genomics* 4:560–569 (1989).
Barringer et al. *Gene* 89:117–122 (1990).
Stoflet et al. Science 239:491–494 (1988).

|  | I |  | II |
|---|---|---|---|
| HTLV-I | LPQGFKNSP |  | YMDDIL |
| HTLV-II | LPQGFKNSP |  | YMDDIL |
| BLV | LPQGFINSP |  | YMDDIL |
| MuLV | LPQGFKNSP |  | YVDDLL |
| FeLV | LPQGRKNSP |  | YVDDLL |
| MMTV | LPQGMKNSP |  | YMDDIL |
| IAP | LPQGMANSP |  | YMDDIL |
| RSV | LPQGMTCSP |  | YMDDLL |
|  |  | APP. 25 A.A. |  |
| HIV-1 | LPQGNKGSP |  | YMDDLY |
| HIV-2 | LPQGWKGSP |  | YMDDIL |
| SIV | LPQGWKGSP |  | YMDDIL |
| EIAV | LPQGFVLSP |  | YMDDLL |
| CAEV | LPQGWKLSP |  | YMDDIF |
| VISNA | LPQGWKLSP |  | YMDDIY |
| FIV | LPQGWILSP |  | YMDDIL |
| CONSENSUS | LPQGFKNSP |  | YMDDIL |
|  | W G |  | LY |
|  | · L |  |  |

FIGURE 2

| Virus | Amino Acid Sequences | |
|---|---|---|
| Lentiviruses | LV I region | LV II region |
| VISNA | PHPGGLQRKKHVT | WLGFELHPEKWK |
| CAEV | PHPGGLQKKKHVT | WLGFELHPQTWK |
|  |  | (or) WLGYELHRPA |
| HIV-I | PHPAGLKKKKSVT | WMGYELHPDKWT |
| EIAV | PHPGGLIKCKHMT | WLGYQLCPENWK |
| BIV | PYPPGIKECEHLT | WIGFELTPKKWR |
| FIV | PHPAGLQIKKQVT | WMGYELHPETWT |
| SIV | PHPAGLAKRKRIT | WMGYELWPTKWK |

```
Consensus       PHPGGLQR           WLGFELHP
                A   IKK              M  YQ C
                P   IE               I  F  T
                AI  AI                      W
```

| Non-lentiviruses | LV I region | LV II region |
|---|---|---|
| MuLV | NLLSGLPPSHQWY | YLGYLLKEGQRW |
| MMTV | PSPVAVPKGWEII | YLGTHIQGDSVS |
| BLV | PDLTAIPTHPPHI | FLGQMVHNQIVT |
| IAP | PLLSALPQDWKLI | YLGYKLGSTYVA |
| HTLV-I | PDLSSLPTTLAHL | FLGQIISPNHLT |
| HTLV-II | PDLTSLPTALPHL | FLGQVISPNHLT |

[-----]
approximately
110-140 A.A.

FIGURE 3

| Lentivirus | LV I Nucleotide Sequence (5' to 3') |
|---|---|
| VISNA | CCGCATCCAGGAGGATTACAGAGAAAGAAACATGTAACA |
| CAEV | CCGCATCCGGGAGGACTACAAAAGAAAAAACATGTTACA |
| HIV-I | CCACATCCCGCAGGGTTAAAAAAGAAAAAATCAGTAACA |
| EIAV | CCTCACCCGGGAGGATTAATTAAATGTAAACACATGACT |
| FIV | CCTCATCCTGCTGGTCTACAAATAAAAAAACAAGTAACA |
| SIV | CCACACCCTGCAGGACTAGCAAAAGGAAAAGGATTACA |
| Consensus | CCGCACCCNGGAGGACTA<br>  T  T     CG  CT<br>  A         T  T |

| Lentivirus | LV II Nucleotide Sequence (5' to 3') |
|---|---|
| VISNA | TGGCTTGGATTTGAATTGCATCCGGAGAAATGGAAA |
| CAEV | TGGCTAGGATTTGAACTACACCCGCAGACCTGGAAA |
| HIV-I | TGGATGGGTTATGAACTCCATCCTGATAAATGGACA |
| EIAV | TGGCTAGGTTATCAACTTTGTCCTGAAAATTGGAAA |
| FIV | TGGATGGGTTATGAATTACATCCATTAACATGGACA |
| SIV | TGGATGGGGTACGAATTGTGGCCGACAAAATGGAAG |
| Consensus | TGGATGGGTTATGAACTNCGTCCGGAAAAATGGAAA<br>    C A  G TCC  T   TAG  TTTT CT     CG<br>     T   A                           AACG |

FIGURE 4

| lentivirus | LV I 5' to 3' | LPQG 5' to 3' | YMDD 5' to 3' | LV II 3' to 5' |
|---|---|---|---|---|
| EIAV | 2519-2539 | 2681-2693 | 2783-2794 | 2953-293 |
| FIV | 2316-2636 | 2778-2789 | 2880-2891 | 3037-301 |
| VISNA | 2396-2416 | | 2663-2674 | 2818-279 |
| HIV-1 | 2414-2433 | | 2678-2689 | 2835-281 |

Figure 5

LENTIVIRUS-SPECIFIC NUCLEOTIDE PROBES AND METHODS OF USE

The United States government has rights in this invention by virtue of grants from the National Institutes of Health Nos. RR 03121, RR 01180, R35 CA44356, and T32 AI07233. This is a continuation of copending application Ser. No. 07/746,706, filed on Aug. 16, 1991, now abandoned.

BACKGROUND OF THE INVENTION

The present invention relates to the field of molecular virology and more particularly to nucleic acid probes for detection of viruses.

Viral infections and virus-related diseases are significant medical problems which cause personal pain and suffering as well as great economic hardship to individuals, families, and society. Of particular concern are retroviruses, including human immunodeficiency virus (HIV), the virus causing acquired immunodeficiency syndrome or AIDS.

Retroviruses invade host organisms, such as humans, by attaching to the exterior surface of a host cell and introducing their genetic material, retroviral ribonucleic acid (RNA), into the host cell's cytoplasm. The viral enzyme reverse transcriptase, which is packaged in the virus, generates a DNA copy of the viral genome from the viral RNA. This DNA copy usually integrates into the host cell genome where it is chemically indistinguishable from host cellular DNA. The integrated viral genome is copied by host cell replicative mechanisms and transmitted to the cellular progeny of the infected cell. In addition to replicating the viral DNA, the cellular machinery of the infected host cell transcribes viral DNA into messenger RNA (mRNA) and further translates the viral mRNA into enzymatically active viral proteins. The viral proteins thus formed act within the host cell to produce additional viable and infectious virus particles.

The retrovirus family is characterized by the presence of reverse transcriptase in the virions. This family is composed of several genera including oncovirus, spumavirus, and lentivirus. The typical retrovirus genome is short, generally less than 10 kilobases in length, and simple, usually consisting of only a few genes. The major genes of the retroviral genome are gag, pol, and env, as shown in FIG. 1, which encode structural capsid proteins, reverse transcriptase and related replication proteins, and viral extra-cellular envelope protein components, respectively.

The Lentivirus genus includes HIV and related viruses, some causing immunodeficiency-like disease. Lentiviruses are often distinguished by their ability to cause slowly developing diseases characterized by a long incubation period and protracted course of illness. These viruses often latently infect monocytes and macrophages and then spread to other cells. Lentiviruses generally have a bar-shaped rather than a spherical nucleoid. The genome of lentiviruses normally use a $tRNA^{bys}$ as a primer for negative strand synthesis rather than $tRNA^{pro}$, which is used by most other infectious mammalian retroviruses except spumaviruses and mouse mammary tumor viruses. The reverse transcriptases of lentiviruses are magnesium dependent while mammalian C type viruses (oncoviruses) prefer manganese. Also, lentiviruses are known for their genome complexity in that the genome contains additional genes such as the additional regulatory genes.

Lentiviruses in general, and HIV in particular, are known to mutate frequently and to have tremendous evolutionary potential. In addition, numerous variants of HIV and related immunodeficiency-like lentiviruses probably exist that have not been isolated, studied, or characterized. Such unidentified strains may be responsible for clinical immunodeficiency or other disorders not attributable to currently known lentiviruses.

One of the major problems in the diagnosis of such immunodeficiency disorders is the identification and characterization of the causative agent, the lentiviral genome, which constitutes only a very small fraction of the total genetic material in the patient's body. It is extremely difficult to distinguish such a minute amount of viral related genetic material from the great bulk of normal cellular genetic material contained in the host cell.

One recently developed approach for the detection of retroviral genomes employs the polymerase chain reaction (PCR), as described in U.S. Pat. Nos. 4,683,195 and 4,683,202 to Mullis. PCR has emerged as a powerful and sensitive procedure for the amplification of specific DNA sequences (given proper oligonucleotides for use as primers for the reaction), and as such is a valuable diagnostic tool for the identification and characterization of viral diseases. PCR technology requires pairs of dissimilar DNA oligonucleotides (short fragments of DNA sequence) which act as primers to initiate a controlled polymerase reaction which, in turn, amplifies the genomic sequence that lies between the two oligonucleotide binding sites. The polymerase chain reaction employs a heat-stable polymerase (the Taq polymerase) which permits repeated heating and cooling of the reaction mixture. The amplification process is initiated by first heating the reaction mixture to denature (dissociate) the two complementary strands of the double stranded DNA to be amplified. Upon cooling, each single-stranded DNA oligonucleotide hybridizes to a specific region of one or the other of the complementary DNA strands, and acts as a primer for the heat-stable polymerase. The polymerase uses the oligonucleotide primers as starting points for the elongation of a DNA molecule complementary to the template DNA molecule to which each primer is hybridized. Each of the elongating DNA chains grows towards and beyond the distal primer site of the other template strand. By the end of the first cycle two double stranded copies of the intervening genomic sequence lying between the primer binding sites are generated. The cycle is repeated manyfold, exponentially doubling the number of copies each time. In this fashion even a single copy of a specific DNA sequence can be amplified to detectable levels in a relatively short period of time.

The polymerase chain reaction primer selection is limited by three factors. First, the two oligonucleotides must be complementary to sequences found in the template DNA in order for the oligonucleotides to hybridize to the template DNA. Without this initial hybridization step there would be no primer available for the DNA polymerase to use to initiate elongation, and no copy of the DNA sequence could be made. Second, the primers should hybridize to discrete and unique regions of the template DNA. If the primers hybridize to multiple different sites in the template sequence then the initiation site for elongation, and the DNA copy produced, would vary from cycle to cycle depending upon to which binding site the primer hybridized. Third, the two primer binding sites must not be too distant from one another. The elongation step optimally produces fragments up to approximately 2500 bases in length, and DNA sequences of greater length are amplified less efficiently or not at all. If chain elongation terminates before the distal primer site is incorporated into the sequence, the resultant incomplete DNA molecule will not participate in subsequent rounds of amplification.

While highly specific and unique oligonucleotide primers are desirable to eliminate multiple site hybridization in DNA from a single particular source, such restrictions require that separate primer pairs must be developed for each type of DNA to be probed. For example, an oligonucleotide primer pair that hybridizes to sites in the gag gene of one retrovirus may not hybridize to a similar region in the gag gene of another retrovirus. This is because of the inherent degeneracy of the genetic code (variability in the third base position of each codon), genetic variability from virus to virus, and the highly mutable character of the viral genome. Accordingly, either a mix of the appropriate primers must be used simultaneously in a single test, or else a series of separate tests, each using different primer pairs, must be conducted to screen a biological sample, such as a human patient sample, for the presence of viral gene sequences.

In order to be able to screen a biological sample for the presence of multiple retroviruses in a single test, using a single set of oligonucleotides, "universal retroviral primers" have been developed. Universal primers are degenerate in nature such that they will hybridize to, and serve as primers for the elongation of, functionally identical DNA sequences that are disparate at the actual base sequence level but which share sequence similarity in given regions. For example, even though the actual base sequences of retroviral gag genes are not exactly the same from strain to strain, most codons within conserved regions of the DNA sequence code for the same amino acid. Further, codons are degenerate in the third base position, creating further non-identity of DNA sequence from virus to virus. The majority of codons, and thus the majority of the DNA gene sequence, will be the same from strain to strain, and degenerate primers can be designed that take advantage of this feature such that they will hybridize with any of a variety of similar or related gene sequences.

This approach is appropriate, however, only for related families of genes that share conserved regions of DNA sequence. Primers that are "universal" for all of the retroviruses correspond and hybridize to gene sequences that are conserved throughout all of the retroviruses. Such universal retroviral primers which are capable of detecting all retroviruses generally are known in the art. These "universal retroviral primers" are capable of detecting a wide range of retroviruses by binding to highly conserved core regions of retroviral genomes.

For example, Donehower, et al., "The Use of Primers from Highly Conserved pol Regions to Identify Uncharacterized Retroviruses by the Polymerase Chain Reaction", *J. Virol Methods,* 28:33–46 (1990), describe DNA oligonucleotides directed to either end of a 135 basepair region of the pol gene that is highly conserved across all of the retroviruses. Similar primers directed to the same tyrosine-methionine-aspartic acid-aspartic acid (YMDD) tetrapeptide coded at the 3' end of the pol fragment, and the same leucine-proline-glutamine-glycine (LPQG) tetrapeptide coded at the 5' end of the fragment, have been described by Mack and Sninsky, in "A Sensitive Method for the Identification of Uncharacterized Viruses Related to Known Virus Groups: Hepadnavirus Model System", *Proc. Natl Acad. Sci., USA* 85:6977–6981 (1988). Primers that hybridize to the sequence encoding the tyrosine-methionine-aspartic acid-aspartic acid (YMDD) tetrapeptide are designated herein as "RV I" (an abbreviation for retrovirus primer I), and primers that hybridize to the sequence encoding the leucine-proline-glutamine-glycine (LPQG) tetrapeptide are designated herein as "RV II" (an abbreviation for retrovirus primer II).

Conversely, primers designed to detect exclusively a subfamily of retroviruses, such as lentiviruses, must correspond and hybridize to gene sequences that are conserved in lentiviruses only and which are not present in non-lentiviral viruses. No such oligonucleotide primer pairs, specific for and limited to the exclusive detection of viruses classified in the lentivirus subfamily of retroviruses, are currently known.

There are at least three requirements for lentiviral-specific nucleic acid oligonucleotides. The oligonucleotide sequence must include a gene sequence that is conserved throughout the lentivirus subfamily. The lentivirus-specific oligonucleotides must not hybridize to non-lentivirus DNA sequences, i.e. they must not hybridize to sequences found in other, non-lentiviral, retroviruses. Finally, lentivirus-specific PCR primer pairs must hybridize to gene sequences that are not so far removed from one another as to be ineffective or unable to function in the polymerase chain reaction or in other similar methods for amplification and detection of nucleic acid sequences.

A variety of methods for the amplification and detection of small, single copy gene sequences recently have been, or are being, developed. General reviews of these methods have been prepared by Landegren, U., et al., *Science* 242:229–237 (1988) and Lewis, R., *Genetic Engineering News* 10:1, 54–55 (1990). These methods include polymerase chain reaction (PCR), PCR in situ, ligase amplification reaction (LAR), ligase hybridization, Qβ bacteriophage replicase, transcription-based amplification system (TAS), genomic amplification with transcript sequencing (GAWTS), nucleic acid sequence-based amplification (NASBA) and in situ hybridization. RNA oligonucleotides can be utilized in systems such as the Qβ replicase amplification system to detect lentiviral genomic sequences present in test samples. While PCR and other amplification technology is relatively straightforward and simple, the difficult task is the identification and selection of viral sequences that are unique to and specific for the particular subfamily of viruses to be detected.

Detection and diagnostic kits using lentiviral-specific nucleic acid oligonucleotides would be useful in specifically identifying lentiviral infections. The diagnostic kits currently available are only able to distinguish individual or specific viruses such as human immunodeficiency virus (HIV), not the viral subfamily involved. Lentiviral-specific nucleic acid oligonucleotides would also be useful in identifying and characterizing new and unknown lentiviral strains. This is a particularly important feature since HIV and other lentiviruses are highly mutable. For example, such oligonucleotides would be useful in testing individuals who have diseases clinically suggestive of HIV infection or AIDS, but who are HIV-negative by conventional tests. In addition, such oligonucleotides would provide independent confirmation of HIV-positive results derived from conventional tests. Such oligonucleotides would also be useful in detecting lentiviruses of other species, such as feline immunodeficiency virus, and lentiviral-like cellular sequences.

It is therefore an object of the present invention to provide nucleic acid oligonucleotide probes that are specific for lentiviruses but will not hybridize to retroviruses outside of the lentivirus subfamily.

It is a further object of the present invention to provide degenerate nucleic acid oligonucleotide probes that are specific for lentiviruses but will not hybridize to retroviruses outside of the lentivirus subfamily.

It is a further object of the present invention to provide RNA anti-sense probes that block or regulate lentiviral gene expression and can be used therapeutically to terminate lentiviral transcription, translation, or replication.

It is a further object of the present invention to provide DNA or RNA oligonucleotide primer pairs that hybridize to lentiviral-specific regions of the pol gene such that the DNA or RNA oligonucleotides act as effective primers in DNA or RNA amplification systems.

It is a further object of the present invention to provide DNA oligonucleotide primer pairs that hybridize to lentiviral-specific regions of the pol gene such that the DNA oligonucleotides act as effective primers in DNA amplification systems such as the polymerase chain reaction and similar techniques.

It is yet another object of the present invention to provide RNA oligonucleotides which hybridize to lentiviral-specific regions of the pol gene such that the RNA oligonucleotides act as probes in RNA amplification systems such as the Qβ replicase reaction and similar techniques.

It is still another object of the present invention to provide a method for rapid and specific detection of lentiviral gene sequences in biological materials.

SUMMARY OF THE INVENTION

DNA and RNA oligonucleotides capable of hybridizing to lentiviral-specific conserved regions of the pol gene found in a wide variety of lentiviral genomic sequences, and methods of use thereof, are disclosed. Degenerate nucleic acid oligonucleotides are useful as probes and as primers in DNA and RNA amplification systems such as the polymerase chain reaction and Qβ replicase systems. An important feature of the DNA and RNA oligonucleotides is that they hybridize to a broad range of lentiviral genomes but do not hybridize to the genomes of other types of retroviruses, making them useful for the selective, specific, and exclusive detection of lentiviruses. The nucleic acid oligonucleotides hybridize to regions of the pol gene that are relatively conserved throughout the retroviral subfamily of lentiviruses.

BRIEF DESCRIPTION OF THE DRAWINGS

FIG. 2 depicts known internal sequences of the pol gene encompassing amino acid sequences conserved among non-lentiviral retroviruses (top portion) and amino acid sequence structures conserved among lentiviruses (bottom portion). The symbol I represents the region of hybridization of DNA oligonucleotide RV I, and the symbol II represents the region of hybridization of DNA oligonucleotide RV II. These regions are separated by a distance of approximately 25 amino acids. HTLV-I is human T-cell leukemia virus (type I), HTLV-II is human T-cell leukemia virus (type II), BLV is bovine leukemia virus, MuLV is murine leukemia virus, FeLV is feline leukemia virus, MMTV is mouse mammary tumor virus, IAP is intra-cisternal A particle, RSV is rous sarcoma virus, HIV-1 is human immunodeficiency virus (type I), HIV-2 is human immunodeficiency virus (type II), SIV is a simian immunodeficiency virus, EIAV is equine infectious anemia virus, CAEV is caprine arthritis-encephalitis, VISNA is a virus which causes encephalitis in sheep, and FIV is feline immunodeficiency virus.

FIG. 3 depicts pol amino acid sequences from various lentiviral sources and illustrates the regions of lentiviral homology to which the lentivirus probes hybridize. The consensus sequence for each of the degenerate oligonucleotide hybridizing regions is indicated. The top group of viruses are lentiviruses, the lower group non-lentiviral retroviruses. VISNA is a virus which causes encephalitis in sheep, CAEV is caprine arthritis-encephalitis, HIV-1 is human immunodeficiency virus (type I), EIAV is equine infectious anemia virus, BIV is bovine immunodeficiency virus, FIV is feline immunodeficiency virus, and SIV is a simian immunodeficiency virus. MuLV is murine leukemia virus, MMTV is mouse mammary tumor virus, BLV is bovine leukemia virus, RSV is rous sarcoma virus, IAP is intra-cisternal A particle, HTLV-I is human T-cell leukemia virus (type I), and HTLV-II is human T-cell leukemia virus (type II). Each pair of homologous regions is separated by approximately 110–140 amino acids.

FIG. 4 depicts the nucleotide sequences of several lentivirus genomes in the conserved regions identified as LV I and LV II. VISNA is a virus which causes encephalitis in sheep, CAEV is caprine arthritis-encephalitis, HIV-1 is human immunodeficiency virus (type I), EIAV is equine infectious anemia virus, FIV is feline immunodeficiency virus, BIV is a bovine immunodeficiency virus, and SIV is a simian immunodeficiency virus.

FIG. 5 shows the relationship, by nucleotide location, of the lentiviral-specific regions LV I and LV II of four lentiviruses to two regions in the pol gene conserved throughout the retrovirus genome. The conserved nucleotide regions are named LPQG and YMDD for the amino acids which they encode. The four lentiviruses are EIAV (equine infectious anemia virus), FIV (feline immunodeficiency virus), VISNA (a virus which causes encephalitis in sheep) and HIV1 (human immunodeficiency virus [type I]). The nucleotides are numbered from the start of the viral genome.

DETAILED DESCRIPTION OF THE INVENTION

Figure 1:
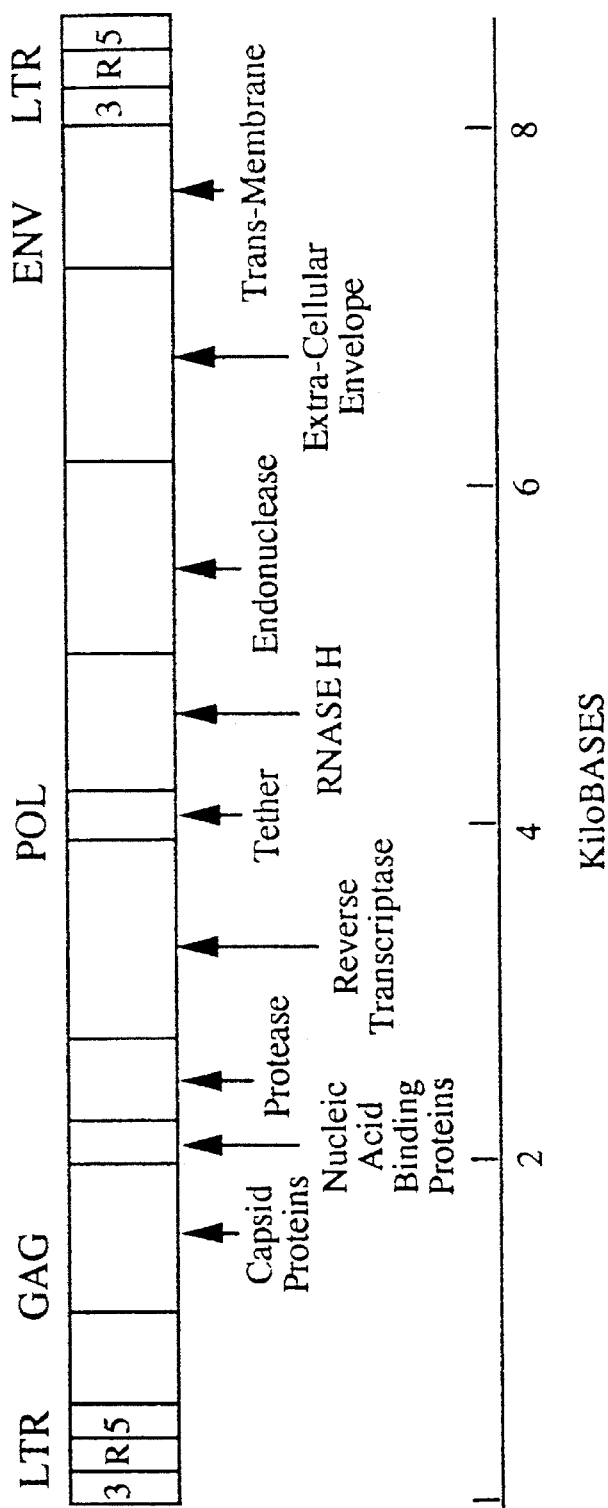
FIG. 1 is a schematic representation of the typical retroviral genomic structure in its double-stranded DNA form. The abbreviation LTR indicates a long terminal repeat. The abbreviations gag, pol, and env designate the genes for structural proteins; protease, reverse transcriptase, a ribonuclease and an endonuclease; and, envelope protein components, respectively. This figure is taken from *The Quarterly Review of Biology*, R. F. Doolittle, D. F. Feng, M. S. Johnson, and M. A. McClure, 64(1):2 (March 1989).

Conserved nucleic acid sequences within the lentiviral genome have been discovered. These sequences are unique to the lentivirus sub-family of retroviruses and are not found in non-lentiviral retroviruses. Oligonucleotide probes and primers have been synthesized which hybridize to these sequences to allow the specific and exclusive detection of lentivirus in a biological sample. The oligonucleotide probes can be used to distinguish lentiviral from non-lentiviral nucleic acid sequences. Preferably a pool of degenerate probes and primers are synthesized to provide greater sensitivity and specificity.

Unlike known universal retroviral probes which hybridize to core homology regions highly conserved across the entire family of retroviruses, the oligonucleotide probes described herein hybridize specifically to lentiviruses. While the universal retroviral probes bind to the amino acid sequences LPQG or YMDD within the pol gene, the lentiviral-specific oligonucleotide probes described herein bind to regions within the pol gene either upstream or downstream from LPQG or YMDD. The oligonucleotide probes are either RNA probes which bind to viral RNA, or DNA probes which bind to viral DNA which has been synthesized from the viral RNA with the aid of the enzyme reverse transcriptase. The degenerate probes either hybridize to virion nucleic acid or proviral DNA which has been incorporated into the DNA of the host cell. Labelled degenerate probes are used to detect lentivirus in a biological sample. The probes also include sequences which can be specifically cleaved by certain restriction endonucleases for purposes of cloning or identification. Furthermore, the probes are used as primers for amplification systems such as the polymerase chain reaction and Qβ replicase systems to cause extensive replication of the portion of the viral genome between the two primers, allowing detection of very small amounts of lentivirus in a biological sample.

Standard abbreviations for nucleotide bases are used herein. C is cytosine, T is thymine, A is adenine, G is guanine, I is inosine, Py is pyrimidine (thymine or cytosine), Pu is purine (adenine or guanine), and N is any nucleotide, either a pyrimidine or purine.

The following standard one letter abbreviations for amino acid sequences are also used herein:

| A | Alanine | R | Arginine | N | Asparagine |
|---|---|---|---|---|---|
| D | Aspartic Acid | C | Cysteine | Q | Glutamine |
| E | Glutamic Acid | G | Glycine | H | Histidine |
| I | Isoleucine | L | Leucine | K | Lysine |
| M | Methionine | F | Phenylalanine | P | Proline |
| S | Serine | T | Threonine | W | Tryptophan |
| Y | Tyrosine | V | Valine | | |
| B | Aspartic Acid or Asparagine | | | | |
| Z | Glutamic Acid or Glutamine | | | | |
| X | Any amino acid | | | | |

The Lentiviral-Specific Sequences

As described above, two highly conserved regions of the pol gene of retroviruses are known to those skilled in the art. These regions have been identified by the amino acids encoded by nucleotides oriented 5' to 3'. The first region, encoding the amino acid sequence leucine-proline-glutamine-glycine (hereinafter the LPQG region or RV I) is located approximately 2681–2789 basepairs downstream from the 5' end of the retroviral genome. The second region, encoding the amino acid sequence tyrosine-methionine-aspartic acid-aspartic acid (hereinafter the YMDD region or RV II) is located approximately 2113–2891 basepairs downstream from the 5' end of the retroviral genome. The YMDD region can be found approximately 25 nucleotides downstream from the LPQG region, as shown in FIG. 2.

The two newly identified lentiviral-specific sequences described herein are also located in the pol gene. These sequences were identified by comparing the DNA sequence for the pol gene from a wide variety of lentiviruses to the DNA sequence for the pol gene from a wide variety of non-lentiviral retroviruses. Each lentiviral-specific nucleotide sequence is approximately 20–40 nucleotides in length. The two sequences are approximately 380–400 nucleotides apart. The first lentiviral-specific sequence, designated LV I, is located approximately 140–150 bases upstream from the LPQG region and 240–250 bases upstream from the YMDD region. Counting from the 5' end of the lentiviral genome, the first lentiviral-specific sequence is located approximately between nucleotide position numbers 2396 and 2636. The second lentiviral-specific sequence, designated LV II, is located approximately 230–250 bases downstream from the LPQG region and 120–140 bases downstream from the YMDD region. Counting from the 5' end of the lentiviral genome, the second lentiviral-specific sequence is located approximately between nucleotide position numbers 2798 and 3037.

The regions of lentiviral homology in the amino acids encoded by the two nucleotide sequences are illustrated in the uppermost portion of FIG. 3. The consensus sequences are set forth in the center portion of FIG. 3. Amino acid sequences of the same regions of non-lentiviral retroviral genomes are not homologous, as shown in the lower portion of FIG. 3.

Synthesis of Degenerate Oligonucleotides

A number of oligonucleotides have been synthesized which bind to the lentivirus-specific homologous regions of the lentiviral RNA or DNA genome. These oligonucleotides are used as probes for the detection of lentiviral RNA or DNA in a sample or are used as primers for amplifying the RNA or DNA spanning the region, approximately 450 nucleotide bases long, between the primers. Methods for synthesizing oligonucleotides are well known in the art. (See, for example, the article by Narang, S.A., "DNA synthesis" *Tetrahedron* 39:3 [1983] which is incorporated by reference herein and the article by Itakura, et al., "Synthesis and use of synthetic oligonucleotides." *Annu. Rev. Biochem.* 53:323 [1984], incorporated by reference herein.) Fully automated systems have been developed and are commercially available. For example, an automated synthesizer from a company such as Applied Biosystems, Inc. (Foster City, Calif.) can be used in accordance with the manufacturer's instructions. Furthermore, there are several companies that will produce unique and specific oligonucleotides on a contractual basis.

Additional potentially useful DNA oligonucleotide probes can be designed and synthesized by one of ordinary skill in the art upon learning the amino acid or nucleotide sequence of the lentiviral-specific conserved region identified herein. RNA oligonucleotide probes are then synthesized from the DNA oligonucleotides by, for example, using an RNA polymerase. The DNA sequences of the lentiviral-specific conserved region for six lentiviruses and consensus sequences are shown in FIG. 4.

Degenerate oligonucleotide probes are often needed because of the degeneracy of the genetic code. There are 64 possible codons, each containing three nucleotides, which encode only 20 amino acids, causing most amino acids to be encoded by more than one codon. Thus, a particular sequence of amino acids can be encoded by several oligonucleotide sequences. Preferably, the probes described herein are pools of degenerate oligonucleotide sequences which will hybridize to the lentivirus-specific regions LV I and LV II of all lentiviruses even though the amino acid and nucleotide sequences of these conserved regions are not identical from virus to virus within the lentivirus sub-family.

The probe or degenerate probes hybridizing to the lentiviral-specific conserved region known as LV I preferably bind to nucleotides within the lentiviral genome which encode the amino acid sequence:

$PHPX_1GLX_2KX_3X_3X_4X_5T$ wherein $X_1$=A, P or G, $X_2$=K or A, $X_3$=K or R, $X_4$=S or R, and $X_5$=V or I. This sequence is designated SEQ ID NO:1 in the Sequence Listing.

The probe or degenerate probes hybridizing to the lentiviral-specific conserved region known as LV II preferably bind to nucleotides within the lentiviral genome which encode the amino acid sequence:

$WX_1GX_2X_3LX_4PX_5KWX_6$ wherein $X_1$=M, L or I; $X_2$=Y, F or T; $X_3$=E or Q; $X_4$=H or W; $X_5$=D or T; and $X_6$=T or K. Most preferably, $X_3$=E. This sequence is designated SEQ ID NO:2 in the Sequence Listing.

It will be understood by those skilled in the art that the probe or degenerate probes hybridizing to LV I or LV II include probes that bind to nucleotides complementary to the nucleotides which encode the amino acid sequences set forth above. It will be further understood by those skilled in the art that the probes or degenerate probes hybridizing to LV I or LV II include probes that bind to nucleotides which encode any of the lentiviral amino acid sequences or consensus amino acid sequences set forth in FIG. 3.

The probe or degenerate probes hybridizing to the lentivirus-specific conserved region known as LV I preferably hybridize to the following nucleotide sequence:

$5'-CCX_1CAX_2CCNGX_3X_4GGX_5X_2TA-3'$ wherein $X_1$=G, T or A; $X_2$=T or C; N is any nucleotide, $X_3$=G or C, $X_4$=A, G or T; and $X_5$=A, C or T. Most preferably, $X_4$=A and $X_5$=A. This sequence is designated SEQ ID NO: 3 in the Sequence Listing.

The probe or degenerate probes hybridizing to the lentivirus-specific conserved region known as LV II preferably hybridize to the following nucleotide sequence:

$5'-TGGX_1TX_2GGX_3TX_4X_5X_6AAX_7TNX_7X_8-3'$ wherein $X_1$=A or C; $X_2$=G, T or A; $X_3$=G, T or A; $X_4$=A or T; $X_5$=T or C; $X_6$=G or C; $X_7$=T or C; N is any nucleotide; and $X_8$=G or A; Most preferably, $X_2$=G; $X_3$=T; $X_4$=A; and $X_5$=T. This sequence is designated SEQ ID NO:4 in the Sequence Listing.

It will be understood by those skilled in the art that the probe or degenerate probes hybridizing to the lentivirus-specific conserved regions known as LV I and LV II include DNA or RNA probes that hybridize to complementary sequences of DNA or RNA sequences of the nucleotide sequences set forth above. It is well known that DNA sequences contain thymine (T) whereas RNA sequences contain uracil (U). It will be further understood by those skilled in the art that the probes or degenerate probes hybridizing to LV I or LV II include probes that bind to nucleotides which encode any of the nucleotide sequences or consensus nucleotide sequences set forth in FIG. 4.

The preferred degenerate oligonucleotide probe hybridizing to the lentiviral-specific conserved region known as LV I is approximately 18–24 bases long, with an approximate degeneracy of 192 and has the nucleotide sequence:

$5'-CCX_1CAX_2CCNGX_3AGGAX_2X_4AX_5AA-3'$ wherein $X_1$=G, T, U, A or I; $X_2$=T, U, C or I; N is any nucleotide; $X_3$=G, C or I; $X_4$=T or U; and $X_5$=C, A or I. This sequence is designated SEQ ID NO:5 and SEQ ID NO:7 in the Sequence Listing.

The preferred degenerate oligonucleotide probe hybridizing to the lentiviral-specific conserved region known as LV II is approximately 17–23 bases long, with an approximate degeneracy of 128 and has the nucleotide sequence:

$5'-X_1X_2NAX_2X_3X_3X_4AX_3AACCCAX_5CCA-3'$ wherein $X_1$=T, U, C or I; $X_2$=A, G or I; N is any nucleotide; $X_3$=T or U; $X_4$=C, A, T, U or I; and $X_5$=G, T, U or I. This sequence is designated SEQ ID NO:6 and SEQ ID NO:8 in the Sequence Listing.

It will be understood by those skilled in the art that the nucleotides in the oligonucleotide probe can be ribonucleotides, deoxyribonucleotides, dideoxyribonucleotides, deazanucleotides, azidonucleotides, or other nucleotide or nucleoside derivatives. It will be further understood by those skilled in the art that the probe or degenerate probes hybridizing to the lentivirus-specific conserved regions known as LV I and LV II include DNA or RNA probes which have sequences complementary to the DNA or RNA sequences of the nucleotide sequences set forth above. It will also be understood that the probes include nucleotide sequences in which any base is replaced by inosine (I). The probes can also be shorter or longer than the probes set forth above as long as hybridization to the lentiviral-specific conserved regions occurs for a sufficient period of time to allow amplification or detection by methods such as those described below. The probes can include restriction sites at either end for purposes of cloning and identification. For example, the sequence CCGGAT is added to the 5' end of the LV I probe, whereas the sequence GGTCTAGA is added to the 5' end of the LV II probe.

A single oligonucleotide probe sequence can be used, however, a degenerate mixture or pool of probes is preferred because the pool creates increased specificity for the conserved amino acid sequence of the lentiviral genome that might be encoded by different nucleotides in different lentiviruses due to the degeneracy of the genetic code.

Methods of Detection Using the Lentiviral-Specific Probes

Once synthesized, the oligonucleotide probes can be used to detect lentiviral sequences in biological samples. In a preferred embodiment, the probes are labelled in such a way that, after hybridization of the probe to nucleic acid sequences in the sample, detection of the label by conventional methods known to those skilled in the art indicates the presence of the lentivirus sequence in the sample. Hybridization can be in vitro or in situ. The method of in situ hybridization is described by Haase, A., et al. "Detection of viral nucleic acids by in situ hybridization", In: *Methods in Virology* (Eds. K. Maramorosch & H. Koprowski) Vol. 7, pp.189–226, Academic Press, New York, 1984, which is incorporated by reference herein and Haase, A. T., et al., "Analysis of viral infections by in situ hybridization", In: *In situ Hybridization—Applications to Neurobiology* (Eds. K. Valentine, J. Roberts & J. Barchas), pp. 197–219, Oxford University Press [Symposium Monograph], Fairlawn, N.J., 1986, which is also incorporated by reference herein.

The various types of labels and methods of labelling nucleotide sequences are well known to those skilled in the art. Several specific labels or reporter groups are set forth below.

For example, the label can be a radiolabel such as, but not restricted to, $^{32}$P, $^{3}$H, $^{14}$C, $^{35}$S, $^{125}$I, or $^{131}$I. A $^{32}$P label can be incorporated into the sequence of the probe by nick-translation, end-labelling or incorporation of labelled nucleotide. A $^{3}$H, $^{14}$C or $^{35}$S label can be incorporated into the sequence of the probe by incorporation of a labelled precursor or by chemical modification. An $^{125}$I or $^{131}$I label can be incorporated into the sequence of the probe by chemical modification. Detection of a label can be by methods such as scintillation counting, gamma ray spectrometry or autoradiography.

The label can also be a Mass or Nuclear Magnetic Resonance (NMR) label such as, for example, $^{13}$C, $^{15}$N, or $^{19}$O. Detection of such a label can be by Mass Spectrometry or NMR.

Dyes and fluorogens can also be used to label the probes. Examples of dyes include ethidium bromide, actidines, propidium and other intercalating dyes, and 4',6'-diamidino-2-phenylindole (DAPI)(Sigma Chemical Company, St. Louis, Mo.) or other proprietary nucleic acid stains. Examples of fluorogens include fluorescein and derivatives, phycoerythrin, allo-phycocyanin, phycocyanin, rhodamine, Texas Red or other proprietary fluorogens. The fluorogens are generally attached by chemical modification. The dye labels can be detected by a spectrophotometer and the fluorogens can be detected by a fluorescence detector.

The probe can alternatively be labelled with a chromogen to provide an enzyme or affinity label. For example, the probe can be biotinylated so that it can be utilized in a biotin-avidin reaction which may also be coupled to a label such as an enzyme or fluorogen. The probe can be labelled with peroxidase, alkaline phosphatase or other enzymes giving a chromogenic or fluorogenic reaction upon addition of substrate. For example, additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used.

Recognition sites for enzymes, such as restriction enzyme sites, can also be incorporated into the probes to provide a detectable label. A label can also be made by incorporating any modified base or precursor containing any label, incorporation of a modified base containing a chemical group recognizable by specific antibodies, or by detecting any bound antibody complex by various means including immunofluorescence or immuno-enzymatic reactions. Such labels can be detected using enzyme-linked immunoassays (ELISA) or by detecting a color change with the aid of a spectrophotometer.

It will be understood by those skilled in the art that other reporter groups can also be used. A review of nucleic acid labels can be found in the article by Landegren, et al., "DNA Diagnostics-Molecular Techniques and Automation", *Science* 242:229–237 (1988) which is incorporated herein by reference.

Amplification of the Lentiviral Sequence with Lentiviral Specific Primers

In a second preferred embodiment, the lentiviral-specific probes are used as single primers or in pairs as primers to amplify lentiviral DNA or RNA in a sample. The primers are used in conjunction with any applicable amplification technology to vastly amplify the lentiviral nucleotide sequences located between the primers to detectable levels. Examples of applicable amplification systems that currently exist or are being developed include polymerase chain reaction (PCR), PCR in situ, ligase amplification reaction (LAR), ligase hybridization, Qβ bacteriophage replicase, transcription-based amplification system (TAS), genomic amplification with transcript sequencing (GAWTS) and nucleic acid sequence-based amplification (NASBA).

PCR technology is described in *PCR Protocols A Guide to Methods and Applications* by Michael A. Innis, David H. Gelfand, John J. Sninsky and Thomas J. White, pp. 39–45 and 337–385 (Academic Press, Inc., Harcourt Brace Jovanovich, Publishers, 1990), the teachings of which are incorporated by reference herein. PCR technology is also described by Marx, J. L., *Science* 140:1408–1410 (1988) and in U.S. Pat. Nos. 4,683,195 and 4,683,202, to Mullis, the teachings of which are also incorporated herein by reference.

PCR using one primer is described by Loh, E. Y., et al., *Science* 243:217 (1989), the teachings of which are incorporated herein by reference. This technique is often used with cDNA (DNA derived from messenger RNA by reverse transcriptase). There are also asymmetric PCR systems and other methods that use one primer or vast excess of one primer. These methods generate mostly single-stranded DNA, suitable for direct sequencing. Single primers can also be used with random hexamers (a degenerate mixture of all or most of the possible DNA hexamers) so that at least one hexamer will act as a second primer by hybridizing somewhere along the sequence at a distance from the first primer.

PCR in situ is the use of PCR amplification on cells or tissue sections followed by detection using in situ hybridization. This technique is described by Haase, A. T., et al., "Amplification and detection of lentiviral DNA inside cells", *Proc. Natl. Acad. Sci. (USA)* 87:4971–4975 (July 1990).

Ligase amplification reaction is described by Wu, D. Y. and Wallace, R. B., *Genomics* 4:560–569 (1989) and Barringer, K. J., et al., *Gene* 89:117–122 (1990), the teachings of which are incorporated herein by reference. Ligase hybridization is described by Landegren, U., et al., *Science* 241:1077–1080 (1988), the teachings of which are incorporated herein by reference.

The Qβ bacteriophage replicase system is described by Kramer, F. R. and Lizardi, P. M., "Replicatable RNA reporters", *Nature* 339:401–402 (1989); Lizardi, P. M., et al., "Exponential amplification of recombinant-RNA hybridization probes", *Bio/Technology* 6:1197–1202 (1988); Lomeli, H., et al., "Quantitative assays based on the use of replicatable hybridization probes", *Clin. Chem.* 35:1826–1831 (1989); and Chu, B. C. F, et al., *Nucl. Acids Res.* 14:5591–5603 (1986), the teachings of which are incorporated herein by reference.

TAS is described by Kwoh, D. Y., et al., *Proc. Natl. Acad. Sci. USA* 86:1173–1177 (1989), the teachings of which are incorporated herein by reference. GAWTS is described by Stoflet, E. S., et al., *Science* 239:491–494 (1988), the teachings of which are incorporated herein by reference. NASBA is described by Compton, J., *Nature* 350:91–92 (1991), the teachings of which are incorporated herein by reference.

Detection and analysis of the nucleotide fragments, amplified by one of the methods described above, are accomplished by standard methods including, for example, gel electrophoresis, dot blots, slot blots and colorimetry, as described in standard laboratory textbooks such as Sambrook, Frisch & Maniatis, *Molecular Cloning: A Laboratory Manual*, 2nd Ed., (Cold Spring Harbor Laboratory, N.Y. 1989), the teachings of which are incorporated herein by reference.

The viral DNA fragment resulting from the amplification using the lentiviral-specific primers is approximately 450 bases long and encompasses both the smaller, highly conserved retroviral core and lentiviral specific sequences. In contrast, the retroviral DNA fragment amplified by using the "universal" retroviral primers is only approximately 135 bases long.

A portion of the DNA amplified by the primers can be further amplified by a "nested" primer set composed of primers that hybridize to regions within the amplified DNA segment. Preferably, the RV I and RV II universal retrovirus primers are used after amplification with primers LV I and LV II to further identify and confirm that the amplified DNA is a portion of a retrovirus genome.

Use of the Lentiviral-Specific Probes

The oligonucleotide probes are used to detect a wide variety of lentiviruses including HIV and related immunodeficiency-like viruses in any population and any species. The probes are also useful in screening for new viruses or cellular sequences related to HIV.

For example, the probes are used to test biological samples from individuals who have already been tested for HIV. These additional tests can be used to confirm or contradict either a former HIV-negative or HIV-positive test result. A person may test negative for HIV, yet exhibit symptoms clinically suggestive of HIV infection or AIDS. Such a person could have an immunodeficiency disorder caused by another virus or could be infected with a mutant form of HIV that is not detectable by conventional tests. The probes are therefore used to determine whether or not the disorder is caused by a lentiviral infection.

The probes are used to screen and further characterize newly identified viruses while more specific detection systems are being developed. The probes are then "fine tuned" for greater specificity after the newly identified virus and its products have been more fully characterized.

The probes are also used to detect present and future HIV variants. HIV is known as a very mutable virus with tremendous and unpredictable evolutionary potential. As the HIV epidemic progresses worldwide, a possible concern is that new variants could arise that are undetectable or poorly detectable by presently available reagents. The probes are capable of detecting the broadest variety of future variants by hybridizing to the least mutable region of the viral genome.

The probes are also used to screen blood products to insure that they are free of lentiviral contamination before being given to patients.

Furthermore, the probes are used as blockers or regulators of lentivirus gene expression by hybridization to lentivirus sense strand RNA. An antisense RNA probe corresponding to one or both of the regions LV I or LV II is synthesized and is incorporated into the lentivirus-infected cell either by transfection with a second virus, or by transformation or microinjection. (A review on antisense RNA by Eguchi, Y., et al., "Antisense RNA", *Ann. Rev. Biochem.* 60:631–652 [1991] is incorporated herein by reference.) The RNA probe either binds to the DNA of the lentivirus and prevents the binding of transcription or replication factors, or the probe binds to and thereby inactivates mRNA so that the amino acid "message" is not made. Alternatively, the probe is attached to a ribozyme. When the probe hybridizes to the appropriate sequence, the ribozyme cleaves it, and terminates replication, transcription, or translation. The engineering of ribozymes is described by Forster, A. C. & Altman, S., "External guide sequences for an RNA enzyme", *Science* 249:783–786 (1990) and is incorporated by reference herein. The technique of terminating replication, transcription, or translation using a ribozyme attached to a probe is described in U.S. Pat. No. 4,987,071 to Cech, T. R., Zaug, A. J., and Been, M.D., issued Jan. 22, 1991, which is incorporated herein by reference.

The present invention will be more fully understood by reference to the following non-limiting examples.

Example 1

Amplification of Lentiviral-Specific DNA Using PCR.

Lentiviral-specific DNA oligonucleotide primers are used in the polymerase chain reaction to amplify lentiviral DNA to levels that are detectable using standard techniques well known to those of ordinarily skill in the art. For example, to a reaction mixture having a final volume of 50 µl, the following components are added:

| | |
|---|---|
| Genomic DNA | 10.00 µl (approx. 1 µg) |
| dNTP mixture | 1.00 µl (50 µM)$_f$ |
| 10X reaction buffer | 5.00 µl |
| TMAC | 0.50 µl (50 µM)$_f$ |
| Taq polymerase | 0.25 µl(0.5 U)$_f$ |
| Primers | 0.50 µl (20 µM)$_f$ |
| Distilled water | 32.75 µl |

The dNTP stock solution concentration is 2.5 mM, resulting in a final concentration of 50 µM for each of the dNTPs. While the addition of tetramethyl ammonium chloride (TMAC) (Fisher Scientific Co., Pittsburgh, Penn.) is optional, better results are obtained with its inclusion. TMAC stock solution is prepared in distilled water at a concentration of 5 mM, resulting in a final concentration of 50 µM. Primers LV I and LV II are synthesized and are supplied in a stock solution at a concentration of 5 µg/µl each, resulting in 25 ng of each primer per reaction mixture.

Lentiviral DNA sequences are amplified by cycling the reaction mixture 36 times through a series of temperature shifts. Best results are obtained when the first cycle consists of 45 seconds at 94° C., followed by one minute at 37° C., which in turn is followed by one minute at 72° C. The subsequent 35 cycles are conducted by incubating the reaction mixture for 30 seconds at 94° C., followed by 45 seconds at 55° C., which in turn is followed by 45 seconds at 72° C.

The reaction product, i.e., the amplified lentiviral gene fragment, is analyzed by standard procedures such as agarose gel electrophoresis. 20 µl of the reaction product is loaded onto an agarose minigel containing ethidium bromide, using commercially obtained reagents, revealing a DNA fragment of approximately 450 bp in length.

Example 2

Amplification of Lentiviral-Specific RNA Using the Qβ Bacteriophage Replicase System.

RNA oligonucleotides corresponding to the DNA sequences of the lentiviral-specific conserved gene sequences are used as probes in the QΩ replicase amplification system. The replicase system entails first attaching a lentiviral-specific RNA to MDV-1 which is a natural template for the replicase enzyme of the Qβ bacteriophage and is commercially available from GeneTrak Systems, Framingham, Mass. This conjugate is then added to the sample to be tested for the presence of lentiviral sequences. The RNA probe conjugated to MDV-1 hybridizes specifically to lentiviral DNA, if present in the sample, forming an RNA:DNA duplex which in turn activates the QΩ replicase.

The Qβ bacteriophage replicase acts upon the RNA:DNA duplex to replicate and amplify the lentiviral RNA sequence to detectable levels. The amplified RNA can be analyzed by standard methods, for example, gel electrophoresis, Northern blotting and colorimetry.

Modifications and variations of the lentiviral specific sequences, and methods of use thereof, will be obvious to those skilled in the art from the foregoing description. Such modifications and variations are intended to come within the scope of the appended claims.

I claim:

1. A probe for detecting the presence of lentiviral nucleic acid comprising an oligonucleotide of at least seventeen nucleotides which hybridizes to a lentivirus nucleic acid sequence in the pol gene specific to and conserved among lentiviruses and does not hybridize to a nucleic acid sequence of retroviruses outside of the lentivirus family, selected from the group consisting of:

5'-$X_1X_2NAX_2X_3X_3X_4AX_3AACCCAX_5CCA$-3' wherein $X_1$=T, U, C or I; $X_2$=A, G or I; N is any nucleotide; $X_3$=T or U; $X_4$=C, A, T, U or I; and $X_5$=G, T, U or I;

3'-$X_1X_2NX_3X_2AAX_4X_3AX_3X_3GGGX_3X_5GGX_3$-5' wherein $X_1$=A, G or I; $X_2$=T, U, C or I; N is any nucleotide; $X_3$=T or U; $X_4$=G, A, T, U or I; and $X_5$=C, A or I;

3'-$X_1X_2NAX_2X_3X_3X_4AX_3AACCCAX_5CCA$-5' wherein $X_1$=T, U, C or I; $X_2$=A, G or I; N is any nucleotide; $X_3$=T or U; $X_4$=C, A, T, U or I; and $X_5$=G, T, U or I;

5'-$X_1X_2NX_3X_2AAX_4X_3AX_3X_3GGGX_3X_5GGX_3$-3' wherein $X_1$=A, G or I; $X_2$=T, U, C or I; N is any nucleotide; $X_3$=T or U; $X_4$=G, A, T, U or I; and $X_5$=C, A or I, and degenerate sequences thereof encoding the amino acid sequence:

$WX_1GX_2X_3LX_4PX_5KWX_6$ wherein $X_1$=M, L or I; $X_2$=Y, F or T; $X_3$=E or Q; $X_4$=H or W; $X_5$=D or T; and $X_6$=T or K and the sequence is designated SEQ ID NO:2 in the Sequence Listing.

2. The probe of claim 1 wherein the lentivirus nucleic acid sequence is located approximately 120–140 nucleotide bases downstream from the sequence encoding the amino acid sequence YMDD, approximately between nucleotide position numbers 2798 and 3037 from the 5' end of the genome.

3. The probe of claim 1 wherein $X_3$=E.

4. A probe for detecting the presence of lentiviral nucleic acid comprising an oligonucleotide of at least seventeen consecutive nucleotide bases which hybridizes to a lentivirus nucleic acid sequence in the pol gene specific to and conserved among lentiviruses and does not hybridize to a nucleic acid sequence of retroviruses outside of the lentivirus family, wherein the lentivirus nucleic acid sequence is:

5'-$CCX_1CAX_2CCNGX_3AGGAX_2X_4AX_5AA$-3' wherein $X_1$=G, T, U, A or I; $X_2$=T, U, C or I; N is any nucleotide; $X_3$=G, C or I; $X_4$=T or U; and $X_5$=C, A or I, designated SEQ ID NO:5 and SEQ ID NO:7 in the Sequence Listing;

3'-$GGX_1GTX_2GGNCX_3TCCTX_2ATX_4TT$-5' wherein $X_1$=C, T, U, A or I; $X_2$=A, G or I; N is any nucleotide; $X_3$=G, C or I; and $X_4$=G, T, U or I, a sequence complementary to SEQ ID NO:5 and SEQ ID NO:7 in the Sequence Listing;

3'-CCX$_1$CAX$_2$CCNGX$_3$AGGAX$_2$X$_4$AX$_5$AA-5' wherein $X_1$=G, T, U, A or I; $X_2$=T, U, C or I; N is any nucleotide; $X_3$=G, C or I; $X_4$=T or U; and $X_5$=C, A or I designated SEQ ID NO:6 and SEQ ID NO:8 in the Sequence Listing; and,

5'-GGX$_1$GTX$_2$GGNCX$_3$TCCTX$_2$ATX$_4$TT-3' wherein $X_1$=C, T, U, A or I; $X_2$=A, G or I; N is any nucleotide; $X_3$=G, C or I; and $X_4$=G, T, U or I, a sequence complementary to SEQ ID NO:6 and SEQ ID NO:8 in the Sequence Listing.

5. The probe of claim 1 wherein the lentivirus nucleic acid sequence is:

5'-TGGX$_1$TX$_2$GGX$_3$TX$_4$X$_5$X$_6$AAX$_7$TNX$_7$X$_8$-3' wherein $X_1$=A or C; $X_2$=G, T or A; $X_3$=G, T or A; $X_4$=A or T; $X_5$=T or C; $X_6$=G or C; $X_7$=T or C; N is any nucleotide; and $X_8$=G or A and the sequence is designated SEQ ID NO:4 in the Sequence Listing.

6. The probe of claim 5 wherein $X_2$=G.
7. The probe of claim 5 wherein $X_3$=T.
8. The probe of claim 5 wherein $X_4$=A.
9. The probe of claim 5 wherein $X_5$=T.
10. The probe of claim 5 wherein $X_7$=T.
11. The probe of claim 5 wherein the oligonucleotide has a sequence selected from the group consisting of:

5'-X$_1$X$_2$NAX$_2$X$_3$X$_3$X$_4$AX$_3$AACCCAX$_5$CCA-3' wherein $X_1$=T, U, C or I; $X_2$=A, G or I; N is any nucleotide; $X_3$=T or U; $X_4$=C, A, T, U or I; and $X_5$=G, T, U or I;

3'-X$_1$X$_2$NX$_3$X$_2$AAX$_4$X$_3$AX$_3$X$_3$GGGX$_3$X$_5$GGX$_3$-5' wherein $X_1$=A, G or I; $X_2$=T, U, C or I; N is any nucleotide; $X_3$=T or U; $X_4$=G, A, T, U or I; and $X_5$=C, A or I;

3'-X$_1$X$_2$NAX$_2$X$_3$X$_3$X$_4$AX$_3$AACCCAX$_5$CCA-5' wherein $X_1$=T, U, C or I; $X_2$=A, G or I; N is any nucleotide; $X_3$=T or U; $X_4$=C, A, T, U or I; and $X_5$=G, T, U or I;

5'-X$_1$X$_2$NX$_3$X$_2$AAX$_4$X$_3$AX$_3$X$_3$GGGX$_3$X$_5$GGX$_3$-3' wherein $X_1$=A, G or I; $X_2$=T, U, C or I; N is any nucleotide; $X_3$=T or U; $X_4$=G, A, T, U or I; and $X_5$=C, A or I.

12. The probe of claim 1 wherein the oligonucleotide is labelled with a detectable label.

13. The probe of claim 12 wherein the label is selected from the group consisting of radiolabels, mass labels, nuclear magnetic resonance labels, dyes, fluorogens, chromogens, recognition sites for enzymes, and modified bases.

14. The probe of claim 1 wherein the probe acts as a primer in combination with reagents for use in an amplification system for the amplification and detection of lentivirus in a biological sample.

15. The probe of claim 14 wherein the amplification system is selected from the group consisting of polymerase chain reaction, polymerase chain reaction in situ, ligase amplification reaction, ligase hybridization, Qβ bacteriophage replicase, transcription-based amplification system (TAS), genomic amplification with transcript sequencing (GAWTS), and nucleic acid sequence-based amplification.

16. A pair of degenerate oligonucleotide primers for amplification and detection of lentivirus in a biological sample comprising a first oligonucleotide which hybridizes to a nucleotide sequence conserved in the lentivirus genome identified as LV I and a second oligonucleotide which hybridizes to a nucleotide sequence conserved in the lentivirus genome identified as LV II, and neither oligonucleotide hybridizes to a nucleic acid sequence of retroviruses outside of the lentivirus family, wherein the first oligonucleotide has a nucleotide sequence selected from the group consisting of:

5'-CCX$_1$CAX$_2$CCNGX$_3$AGGAX$_2$X$_4$AX$_5$AA-3' wherein $X_1$=G, T, U, A or I; $X_2$=T, U, C or I; N is any nucleotide; $X_3$=G, C or I; $X_4$=T or U; and $X_5$=C, A or I; designated SEQ ID NO:5 and SEQ ID NO:7 in the Sequence Listing;

3'-GGX$_1$GTX$_2$GGNCX$_3$TCCTX$_2$ATX$_4$TT-5' wherein $X_1$=C, T, U, A or I; $X_2$=A, G or I; N is any nucleotide; $X_3$=G, C or I; and $X_4$=G, T, U or I; a complementary sequence of SEQ ID NO:5 and SEQ ID NO:7;

3'-CCX$_1$CAX$_2$CCNGX$_3$AGGAX$_2$X$_4$AX$_5$AA-5' wherein $X_1$=G, T, U, A or I; $X_2$=T, U, C or I; N is any nucleotide; $X_3$=G, C or I; $X_4$=T or U; and $X_5$=C, A or I; an inverted sequence of SEQ ID NO:5 and SEQ ID NO:7 and,

5'-GGX$_1$GTX$_2$GGNCX$_3$TCCTX$_2$ATX$_4$TT-3' wherein $X_1$=C, T, U, A or I; $X_2$=A, G or I; N is any nucleotide; $X_3$=G, C or I; and $X_4$=G, T, U or I; an inverted complementary sequence of SEQ ID NO:5 and SEQ ID NO:7; and the second oligonucleotide has a nucleotide sequence selected from the group consisting of:

5'-X$_1$X$_2$NAX$_2$X$_3$X$_3$X$_4$AX$_3$AACCCAX$_5$CCA-3' wherein $X_1$=T, U, C or I; $X_2$=A, G or I; N is any nucleotide; $X_3$=T or U; $X_4$=C, A, T, U or I; and $X_5$=G, T, U or I; designated SEQ ID NO:6 and SEQ ID NO:8 in the Sequence Listing;

3'-X$_1$X$_2$NX$_3$X$_2$AAX$_4$X$_3$AX$_3$X$_3$GGGX$_3$X$_5$GGX$_3$-5' wherein $X_1$=A, G or I; $X_2$=T, U, C or I; N is any nucleotide; $X_3$=T or U; $X_4$=G, A, T, U or I; and $X_5$=C, A or I; a complementary sequence of SEQ ID NO:6 and SEQ ID NO:8; and

3'-X$_1$X$_2$NAX$_2$X$_3$X$_3$X$_4$AX$_3$AACCCAX$_5$CCA-5' wherein $X_1$=T, U, C or I; $X_2$=A, G or I; N is any nucleotide; $X_3$=T or U; $X_4$=C, A, T, U or I; and $X_5$=G, T, U or I; an inverted sequence of SEQ ID NO:6 and SEQ ID NO:8;

5'-X$_1$X$_2$NX$_3$X$_2$AAX$_4$X$_3$AX$_3$X$_3$GGGX$_3$X$_5$GGX$_3$-3' wherein $X_1$=A, G or I; $X_2$=T, U, C or I; N is any nucleotide; $X_3$=T or U; $X_4$=G, A, T, U or I; and $X_5$=C, A or I an inverted complementary sequence of SEQ ID NO:6 and SEQ ID NO:8, and degenerate sequences thereof wherein the conserved nucleotide sequence LV I encodes the amino acid sequence:

PHPX$_1$GLX$_2$GKX$_3$X$_3$X$_4$X$_5$T wherein $X_1$=A, P or G, $X_2$=K or A, $X_3$=K or R, $X_4$=S or R, and $X_5$=V or I, designated SEQ ID NO:1 in the Sequence Listing, and the conserved nucleotide sequence LV II encodes the amino acid sequence:

$$WX_1GX_2X_3LX_4PX_5KWX_6$$

wherein $X_1$=M, L or I; $X_2$=Y, F or T; $X_3$=E or Q; $X_4$=H or W; $X_5$=D or T; and $X_6$=T or K, designated SEQ ID NO:2 in the Sequence Listing, in combination with reagents for use in an amplification system.

17. The primers of claim 16 wherein the amplification system is selected from the group consisting of polymerase chain reaction, polymerase chain reaction in situ, ligase amplification reaction, ligase hybridization, Qβ bacteriophage replicase, transcription-based amplification system (TAS), genomic amplification with transcript sequencing (GAWTS), and nucleic acid sequence-based amplification.

18. The primers of claim 16 wherein $X_3$=E in the sequence LV II.

19. The primers of claim 16 wherein the conserved nucleotide sequence LV I is:

$$5'\text{-}CCX_1CAX_2CCNGX_3X_4GGX_5X_2TA\text{-}3'$$

wherein $X_1$=G, T or A; $X_2$=T or C; N is any nucleotide; $X_3$=G or C; $X_4$=A, G or T; and $X_5$=A, C or T; designated SEQ ID NO:3 in the Sequence Listing, and the conserved nucleotide sequence LV II is:

$$5'\text{-}TGGX_1TX_2GGX_3TX_4X_5X_6AAX_7TNX_7X_8\text{-}3'$$

wherein $X_1$=A or C; $X_2$=G, T or A; $X_3$=G, T or A; $X_4$=A or T; $X_5$=T or C; $X_6$=G or C; $X_7$=T or C; N is any nucleotide; and $X_8$=G or A; designated SEQ ID NO:4 in the Sequence Listing.

20. The primers of claim 19 wherein $X_4$=A in the sequence LV I.

21. The primer of claim 19 wherein $X_5$=A in the sequence LV I.

22. The primer of claim 19 wherein $X_2$=G in the sequence LV II.

23. The primer of claim 19 wherein $X_3$=T in the sequence LV II.

24. The primer of claim 19 wherein $X_4$=A in the sequence LV II.

25. The primer of claim 19 wherein $X_5$=T in the sequence LV II.

26. The primer of claim 19 wherein $X_7$=T in the sequence LV II.

27. The primers of claim 16 wherein the first oligonucleotide has a nucleotide sequence selected from the group consisting of:

$$5'\text{-}CCX_1CAX_2CCNGX_3AGGAX_2X_4AX_5AA\text{-}3'$$

wherein $X_1$=G, T, U, A or I; $X_2$=T, U, C or I; N is any nucleotide; $X_3$=G, C or I; $X_4$=T or U; and $X_5$=C, A or I; designated SEQ ID NO:5 and SEQ ID NO:7 in the Sequence Listing;

$$3'\text{-}GGX_1GTX_2GGNCX_3TCCTX_2ATX_4TT\text{-}5'$$

wherein $X_1$=C, T, U, A or I; $X_2$=A, G or I; N is any nucleotide; $X_3$=G, C or I; and $X_4$=G, T, U or I; a complementary sequence of SEQ ID NO:5 and SEQ ID NO:7;

$$3'\text{-}CCX_1CAX_2CCNGX_3AGGAX_2X_4AX_5AA\text{-}5'$$

wherein $X_1$=G, T, U, A or I; $X_2$=T, U, C or I; N is any nucleotide; $X_3$=G, C or I; $X_4$=T or U; and $X_5$=C, A or I; an inverted sequence of SEQ ID NO:5 and SEQ ID NO:7 and, $$5'\text{-}GGX_1GTX_2GGNCX_3TCCTX_2ATX_4TT\text{-}3'$$

wherein $X_1$=C, T, U, A or I; $X_2$=A, G or I; N is any nucleotide; $X_3$=G, C or I; and $X_4$=G, T, U or I; an inverted complementary sequence of SEQ ID NO:5 and SEQ ID NO:7; and the second oligonucleotide has a nucleotide sequence selected from the group consisting of:

$$5'\text{-}X_1X_2NAX_2X_3X_3X_4AX_3AACCCAX_5CCA\text{-}3'$$

wherein $X_1$=T, U, C or I; $X_2$=A, G or I; N is any nucleotide; $X_3$=T or U; $X_4$=C, A, T, U or I; and $X_5$=G, T, U or I; designated SEQ ID NO:6 and SEQ ID NO:8 in the Sequence Listing;

$$3'\text{-}X_1X_2NX_3X_2AAX_4X_3AX_3X_3GGGX_3X_5GGX_3\text{-}5'$$

wherein $X_1$=A, G or I; $X_2$=T, U, C or I; N is any nucleotide; $X_3$=T or U; $X_4$=G, A, T, U or I; and $X_5$=C, A or I; a complementary sequence of SEQ ID NO:6 and SEQ ID NO:8; and $$3'\text{-}X_1X_2NAX_2X_3X_3X_4AX_3AACCCAX_5CCA\text{-}5'$$

wherein $X_1$=T, U, C or I; $X_2$=A, G or I; N is any nucleotide; $X_3$=T or U; $X_4$=C, A, T, U or I; and $X_5$=G, T, U or I; an inverted sequence of SEQ ID NO:6 and SEQ ID NO:8;

$$5'\text{-}X_1X_2NX_3X_2AAX_4X_3AX_3X_3GGGX_3X_5GGX_3\text{-}3'$$

wherein $X_1$=A, G or I; $X_2$=T, U, C or I; N is any nucleotide; $X_3$=T or U; $X_4$=G, A, T, U or I; and $X_5$=C, A or I an inverted complementary sequence of SEQ ID NO:6 and SEQ ID NO:8.

28. A method of detecting lentiviral nucleic acid in a biological sample comprising:
combining the sample with a first oligonucleotide probe, wherein the first oligonucleotide has a nucleotide sequence selected from the group consisting of:

$$5'\text{-}CCX_1CAX_2CCNGX_3AGGAX_2X_4AX_5AA\text{-}3'$$

wherein $X_1$=G, T, U, A or I; $X_2$=T, U, C or I; N is any nucleotide; $X_3$=G, C or I; $X_4$=T or U; and $X_5$=C, A or I; designated SEQ ID NO:5 and SEQ ID NO:7 in the Sequence Listing;

$$3'\text{-}GGX_1GTX_2GGNCX_3TCCTX_2ATX_4TT\text{-}5'$$

wherein $X_1$=C, T, U, A or I; $X_2$=A, G or I; N is any nucleotide; $X_3$=G, C or I; and $X_4$=G, T, U or I; a complementary sequence of SEQ ID NO:5 and SEQ ID NO:7;

$$3'\text{-}CCX_1CAX_2CCNGX_3AGGAX_2X_4AX_5AA\text{-}5'$$

wherein $X_1$=G, T, U, A or I; $X_2$=T, U, C or I; N is any nucleotide; $X_3$=G, C or I; $X_4$=T or U; and $X_5$=C, A or I; an inverted sequence of SEQ ID NO:5 and SEQ ID NO:7 and, $$5'\text{-}GGX_1GTX_2GGNCX_3TCCTX_2ATX_4TT\text{-}3'$$

wherein $X_1$=C, T, U, A or I; $X_2$=A, G or I; N is any nucleotide; $X_3$=G, C or I; and $X_4$=G, T, U or I; an inverted complementary sequence of SEQ ID NO:5 and SEQ ID NO:7; and a second oligonucleotide has a nucleotide sequence selected from the group consisting of:

5'- $X_1X_2NAX_2X_3X_3X_4AX_3AACCCAX_5CCA$-3' wherein $X_1$=T, U, C or I; $X_2$=A, G or I; N is any nucleotide; $X_3$=T or U; $X_4$=C, A, T, U or I; and $X_5$=G, T, U or I; designated SEQ ID NO:6 and SEQ ID NO:8 in the Sequence Listing;

3'-$X_1X_2NX_3X_2AAX_4X_3AX_3X_3GGGX_3X_5GGX_3$-5' wherein $X_1$=A, G or I; $X_2$=T, U, C or I; N is any nucleotide; $X_3$=T or U; $X_4$=G, A, T, U or I; and $X_5$=A or I; a complementary sequence of SEQ ID NO:6 and SEQ ID NO:8; and

3'-$X_1X_2NAX_2X_3X_3X_4AX_3AACCCAX_5CCA$-5' wherein $X_1$=T, U, C or I; $X_2$=A, G or I; N is any nucleotide; $X_3$=T or U; $X_4$=C, A, T, U or I; and $X_5$=G, T, U or I; an inverted sequence of SEQ ID NO:6 and SEQ ID NO:8;

5'- $X_1X_2NX_3X_2AAX_4X_3AX_3X_3GGGX_3X_5GGX_3$-3' wherein $X_1$=A, G or I; $X_2$=T, U, C or I; N is any nucleotide; $X_3$=T or U; $X_4$=G, A, T, U or I; and $X_5$=C, A or I an inverted complementary sequence of SEQ ID NO:6 and SEQ ID NO:8, and degenerate sequences thereof wherein the conserved nucleotide sequence LV I encodes the amino acid sequence:

PHP$X_1$GL$X_2$K$X_3X_3X_4X_5$T wherein $X_1$=A, P or G, $X_2$=K or A, $X_3$=K or R, $X_4$=S or R, and $X_5$=V or I, designated SEQ ID NO:1 in the Sequence Listing, and the conserved nucleotide sequence LV II encodes the amino acid sequence:

W$X_1$G$X_2X_3$L$X_4$P$X_5$KW$X_6$ wherein $X_1$=M, L or I; $X_2$=Y, F or T; $X_3$=E or Q; $X_4$=H or W; $X_5$=D or T; and $X_6$=T or K, designated SEQ ID NO:2 in the Sequence Listing;

incubating the combination for a sufficient period of time at a temperature which promotes hybridization of the oligonucleotide probe to the lentiviral-specific nucleic acid sequence, not to a nucleic acid sequence of retroviruses outside of the lentivirus family; and detecting hybridization.

29. The method of claim 28 wherein the probe is labelled with a detectable label and hybridization is detected by detecting the label.

30. The method of claim 29 wherein the label is selected from the group consisting of radiolabels, mass labels, nuclear magnetic resonance labels, dyes, fluorogens, chromogens, restriction sites for enzymes, and modified bases.

31. The method of claim 28 further comprising combining the sample and first oligonucleotide probe with a second oligonucleotide probe complementary to a second conserved lentiviral-specific nucleic acid sequence in the pol gene of the lentiviral genome;

adding reagents of a nucleic acid sequence amplification system;

replicating and amplifying the intervening lentiviral nucleic acid sequence by the amplification system, wherein the oligonucleotide probes are primers for the amplification system; and detecting the amplified lentiviral-specific nucleic acid sequence.

32. The method of claim 31 wherein the amplification system is polymerase chain reaction.

33. The method of claim 31 wherein the oligonucleotides are RNA and further comprising attaching the RNA oligonucleotides to an RNA template for Qβ bacteriophage replicase to form a lentiviral-specific template molecule;

combining the template molecule with the sample;

hybridizing the template molecule to any lentiviral-specific DNA sequences within the sample to form an RNA:DNA duplex, incubating the reaction mixture in the presence of Qβ replicase wherein Qβ replicase is activated by the RNA:DNA duplex and acts upon the RNA:DNA duplex to amplify the lentiviral-specific RNA, and detecting the amplified lentiviral-specific RNA.

34. The probe of claim 4 wherein the oligonucleotide is labelled with a detectable label.

35. The probe of claim 4 wherein the probe acts as a primer in combination with reagents for use in an amplification system for the amplification and detection of lentivirus in a biological sample.

36. The probe of claim 34 wherein the label is selected from the group consisting of radiolabels, mass labels, nuclear magnetic resonance labels, dyes, fluorogens, chromogens, recognition sites for enzymes, and modified bases.

37. The probe of claim 1 wherein the probe acts as a primer in combination with reagents for use in an amplification system for the amplification and detection of lentivirus in a biological sample.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: lentivirus ( i x ) FEATURE:
        ( A ) NAME/KEY: Modified-site
        ( B ) LOCATION: 4
        ( D ) OTHER INFORMATION: /note=""X"at position 4 is A, P, or G."

( i x ) FEATURE:
        ( A ) NAME/KEY: Modified-site
        ( B ) LOCATION: 7
        ( D ) OTHER INFORMATION: /note=""X"at position 7 is K or A."

( i x ) FEATURE:
        ( A ) NAME/KEY: Modified-site
        ( B ) LOCATION: 9
        ( D ) OTHER INFORMATION: /note=""X"at position 9 is K or R."

( i x ) FEATURE:
        ( A ) NAME/KEY: Modified-site
        ( B ) LOCATION: 10
        ( D ) OTHER INFORMATION: /note=""X"at position 10 is K or R."

( i x ) FEATURE:
        ( A ) NAME/KEY: Modified-site
        ( B ) LOCATION: 11
        ( D ) OTHER INFORMATION: /note=""X"at position 11 is S or R."

( i x ) FEATURE:
        ( A ) NAME/KEY: Modified-site
        ( B ) LOCATION: 12
        ( D ) OTHER INFORMATION: /note=""X"at position 12 is V or L."

( x i ) SEQUENCE DESCRIPTION: SEQ ID NO:1:

Pro His Pro Xaa Gly Leu Xaa Lys Xaa Xaa Xaa Xaa Thr
    1                    5                              10

( 2 ) INFORMATION FOR SEQ ID NO:2:

( i ) SEQUENCE CHARACTERISTICS:

(A) LENGTH: 12 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: lentivirus (ix) FEATURE:
          (A) NAME/KEY: Modified-site
          (B) LOCATION: 2
          (D) OTHER INFORMATION: /note="″X″at position 2 is M, L, or I."

(ix) FEATURE:
          (A) NAME/KEY: Modified-site
          (B) LOCATION: 4
          (D) OTHER INFORMATION: /note="″X″at position 4 is F or T."

(ix) FEATURE:
          (A) NAME/KEY: Modified-site
          (B) LOCATION: 5
          (D) OTHER INFORMATION: /note="″X″at position 5 is E or Q."

(ix) FEATURE:
          (A) NAME/KEY: Modified-site
          (B) LOCATION: 7
          (D) OTHER INFORMATION: /note="″X″at position 7 is H or W."

(ix) FEATURE:
          (A) NAME/KEY: Modified-site
          (B) LOCATION: 9
          (D) OTHER INFORMATION: /note="″X″at position 9 is D or T."

(ix) FEATURE:
          (A) NAME/KEY: Modified-site
          (B) LOCATION: 12
          (D) OTHER INFORMATION: /note="″X″at position 12 is T or K."

(xi) SEQUENCE DESCRIPTION: SEQ ID NO:2:

Trp  Xaa  Gly  Xaa  Xaa  Leu  Xaa  Pro  Xaa  Lys  Trp  Xaa
    1                   5                        10

(2) INFORMATION FOR SEQ ID NO:3:

(i) SEQUENCE CHARACTERISTICS:
          (A) LENGTH: 18 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: YES (v) FRAGMENT TYPE: internal (vi) ORIGINAL SOURCE:
          (A) ORGANISM: lentivirus (ix) FEATURE:
          (A) NAME/KEY: misc_difference ( B ) LOCATION: replace(3, "")
                    ( D ) OTHER INFORMATION: /note=""N"at position 3 is G, T,
                        A."

( i x ) FEATURE:
                    ( A ) NAME/KEY: misc_difference
                    ( B ) LOCATION: replace(6, "")
                    ( D ) OTHER INFORMATION: /note=""N"at position 6 is T or
                        C."

( i x ) FEATURE:
                    ( A ) NAME/KEY: misc_difference
                    ( B ) LOCATION: replace(9, "")
                    ( D ) OTHER INFORMATION: /note=""N"at position 9 is G, C,
                        A, or T."

( i x ) FEATURE:
                    ( A ) NAME/KEY: misc_difference
                    ( B ) LOCATION: replace(11, "")
                    ( D ) OTHER INFORMATION: /note=""N"at position 11 is G or
                        C."

( i x ) FEATURE:
                    ( A ) NAME/KEY: misc_difference
                    ( B ) LOCATION: replace(12, "")
                    ( D ) OTHER INFORMATION: /note=""N"at position 12 is A, G,
                        or T."

( i x ) FEATURE:
                    ( A ) NAME/KEY: misc_difference
                    ( B ) LOCATION: replace(15, "")
                    ( D ) OTHER INFORMATION: /note=""N"at position 15 is A, C,
                        or T."

( i x ) FEATURE:
                    ( A ) NAME/KEY: misc_difference
                    ( B ) LOCATION: replace(16, "")
                    ( D ) OTHER INFORMATION: /note=""N"at position 16 is T or
                        C."

( x i ) SEQUENCE DESCRIPTION: SEQ ID NO:3:

CCNCANCCNG NNGGNNTA                                                                                                              1 8

( 2 ) INFORMATION FOR SEQ ID NO:4:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
                    ( A ) ORGANISM: lentivirus ( i x ) FEATURE:
                    ( A ) NAME/KEY: misc_difference
                    ( B ) LOCATION: replace(4, "")
                    ( D ) OTHER INFORMATION: /note=""N"at position 4 is A or
                        C."

( i x ) FEATURE:
                    ( A ) NAME/KEY: misc_difference
                    ( B ) LOCATION: replace(6, "")
                    ( D ) OTHER INFORMATION: /note=""N"at position 6 is G, T,
                        or A."

( i x ) FEATURE:
                    ( A ) NAME/KEY: misc_difference
                    ( B ) LOCATION: replace(9, "")

( D ) OTHER INFORMATION: /note=""N"at position 9 is G, T,
                    or A."

( i x ) FEATURE:
                ( A ) NAME/KEY: misc_difference
                ( B ) LOCATION: replace(11, "")
                ( D ) OTHER INFORMATION: /note=""N"at position 11 is A or
                    T."

( i x ) FEATURE:
                ( A ) NAME/KEY: misc_difference
                ( B ) LOCATION: replace(12, "")
                ( D ) OTHER INFORMATION: /note=""N"at position 12 is T or
                    C."

( i x ) FEATURE:
                ( A ) NAME/KEY: misc_difference
                ( B ) LOCATION: replace(13, "")
                ( D ) OTHER INFORMATION: /note=""N"at position 13 is G or
                    C."

( i x ) FEATURE:
                ( A ) NAME/KEY: misc_difference
                ( B ) LOCATION: replace(16, "")
                ( D ) OTHER INFORMATION: /note=""N"at position 16 is T or
                    C."

( i x ) FEATURE:
                ( A ) NAME/KEY: misc_difference
                ( B ) LOCATION: replace(18, "")
                ( D ) OTHER INFORMATION: /note=""N"at position 18 is A, T,
                    G, or C."

( i x ) FEATURE:
                ( A ) NAME/KEY: misc_difference
                ( B ) LOCATION: replace(19, "")
                ( D ) OTHER INFORMATION: /note=""N"at position 19 is T or
                    C."

( i x ) FEATURE:
                ( A ) NAME/KEY: misc_difference
                ( B ) LOCATION: replace(20, "")
                ( D ) OTHER INFORMATION: /note=""N"at position 20 is G or
                    A."

( x i ) SEQUENCE DESCRIPTION: SEQ ID NO:4:

TGGNTGGNT  NNNAANTNNN                                                                                                    20

( 2 ) INFORMATION FOR SEQ ID NO:5:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( v ) FRAGMENT TYPE: internal ( v i ) ORIGINAL SOURCE:
                ( A ) ORGANISM: lentivirus ( i x ) FEATURE:
                ( A ) NAME/KEY: misc_difference
                ( B ) LOCATION: replace(3, "")
                ( D ) OTHER INFORMATION: /note=""N"at position 3 is G, T,
                    A, or I."

( i x ) FEATURE:
                ( A ) NAME/KEY: misc_difference
                ( B ) LOCATION: replace(6, "")
                ( D ) OTHER INFORMATION: /note=""N"at position 6 is T, C,
                    or I."

( i x ) FEATURE:
    ( A ) NAME/KEY: misc_difference
    ( B ) LOCATION: replace(9, "")
    ( D ) OTHER INFORMATION: /note=""N"at position 9 is G, C,
        A, T, or I."

( i x ) FEATURE:
    ( A ) NAME/KEY: misc_difference
    ( B ) LOCATION: replace(11, "")
    ( D ) OTHER INFORMATION: /note=""N"at position 11 is G, C,
        or I."

( i x ) FEATURE:
    ( A ) NAME/KEY: misc_difference
    ( B ) LOCATION: replace(16, "")
    ( D ) OTHER INFORMATION: /note=""N"at position 16 is T, C,
        or I."

( i x ) FEATURE:
    ( A ) NAME/KEY: misc_difference
    ( B ) LOCATION: replace(19, "")
    ( D ) OTHER INFORMATION: /note=""N"at position 19 is C, A,
        or I."

( x i ) SEQUENCE DESCRIPTION: SEQ ID NO:5:

CCNCANCCNG NAGGANTANA A        21

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v ) FRAGMENT TYPE: internal ( v i ) ORIGINAL SOURCE:
        ( A ) ORGANISM: lentivirus ( i x ) FEATURE:
        ( A ) NAME/KEY: misc_difference
        ( B ) LOCATION: replace(1, "")
        ( D ) OTHER INFORMATION: /note=""N"at position 1 is T, C,
            or I."

( i x ) FEATURE:
        ( A ) NAME/KEY: misc_difference
        ( B ) LOCATION: replace(2, "")
        ( D ) OTHER INFORMATION: /note=""N"at position 2 is A, G,
            or I."

( i x ) FEATURE:
        ( A ) NAME/KEY: misc_difference
        ( B ) LOCATION: replace(3, "")
        ( D ) OTHER INFORMATION: /note=""N"at position 3 is A, G,
            T, C, or I."

( i x ) FEATURE:
        ( A ) NAME/KEY: misc_difference
        ( B ) LOCATION: replace(5, "")
        ( D ) OTHER INFORMATION: /note=""N"at position 5 is A, G,
            or I."

( i x ) FEATURE:
        ( A ) NAME/KEY: misc_difference
        ( B ) LOCATION: replace(8, "")
        ( D ) OTHER INFORMATION: /note=""N"at position 8 is C, A,
            T, or I."

( i x ) FEATURE:
        ( A ) NAME/KEY: misc_difference
        ( B ) LOCATION: replace(17, "")

(D) OTHER INFORMATION: /note="'N'at position 17 is G, T, or I."

(xi) SEQUENCE DESCRIPTION: SEQ ID NO:6:

NNNANTTNAT AACCCANCCA 20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: rRNA (iii) HYPOTHETICAL: NO (v) FRAGMENT TYPE: internal (vi) ORIGINAL SOURCE:
        (A) ORGANISM: lentivirus (ix) FEATURE:
        (A) NAME/KEY: misc_difference
        (B) LOCATION: replace(3, "")
        (D) OTHER INFORMATION: /note="'N'at position 3 is G, U, A, or I."

(ix) FEATURE:
        (A) NAME/KEY: misc_difference
        (B) LOCATION: replace(6, "")
        (D) OTHER INFORMATION: /note="'N'at position 6 is U, C, or I."

(ix) FEATURE:
        (A) NAME/KEY: misc_difference
        (B) LOCATION: replace(9, "")
        (D) OTHER INFORMATION: /note="'N'at position 9 is G, C, A, U, or I."

(ix) FEATURE:
        (A) NAME/KEY: misc_difference
        (B) LOCATION: replace(11, "")
        (D) OTHER INFORMATION: /note="'N'at position 11 is G, C, or I."

(ix) FEATURE:
        (A) NAME/KEY: misc_difference
        (B) LOCATION: replace(16, "")
        (D) OTHER INFORMATION: /note="'N'at position 16 is U, C, or I."

(ix) FEATURE:
        (A) NAME/KEY: misc_difference
        (B) LOCATION: replace(19, "")
        (D) OTHER INFORMATION: /note="'N'at position 19 is C, A, or I."

(xi) SEQUENCE DESCRIPTION: SEQ ID NO:7:

CCNCANCCNG NAGGANUANA A 21

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: rRNA (iii) HYPOTHETICAL: NO (v) FRAGMENT TYPE: internal (vi) ORIGINAL SOURCE:
    (A) ORGANISM: lentivirus (ix) FEATURE:
    (A) NAME/KEY: misc_difference
    (B) LOCATION: replace(1, "")
    (D) OTHER INFORMATION: /note="""N""at position 1 is U, C, or I."

(ix) FEATURE:
    (A) NAME/KEY: misc_difference
    (B) LOCATION: replace(2, "")
    (D) OTHER INFORMATION: /note="""N""at position 2 is A, G, or I."

(ix) FEATURE:
    (A) NAME/KEY: misc_difference
    (B) LOCATION: replace(3, "")
    (D) OTHER INFORMATION: /note="""N""at position 3 is A, G, C, U, or I."

(ix) FEATURE:
    (A) NAME/KEY: misc_difference
    (B) LOCATION: replace(5, "")
    (D) OTHER INFORMATION: /note="""N""at position 5 is A, G, or I."

(ix) FEATURE:
    (A) NAME/KEY: misc_difference
    (B) LOCATION: replace(8, "")
    (D) OTHER INFORMATION: /note="""N""at position 8 is C, A, U, or I."

(ix) FEATURE:
    (A) NAME/KEY: misc_difference
    (B) LOCATION: replace(17, "")
    (D) OTHER INFORMATION: /note="""N""at position 17 is G, U, or I."

(xi) SEQUENCE DESCRIPTION: SEQ ID NO:8:

NNNANUUNAU AACCCANCCA                    20